(12) United States Patent
Rada et al.

(10) Patent No.: US 9,095,664 B2
(45) Date of Patent: Aug. 4, 2015

(54) METHOD AND SYSTEM FOR PROVIDING PRIMING AND RESTITUTION LIQUIDS FOR AN EXTRACORPOREAL BLOOD TREATMENT

(75) Inventors: Hiram Rada, Lyons (FR); Nicolas Semenzato, Decines Charpieu (FR)

(73) Assignee: Gambro Lundia AB, Lund (SE)

( * ) Notice: Subject to any disclaimer, the term of this patent is extended or adjusted under 35 U.S.C. 154(b) by 566 days.

(21) Appl. No.: 13/330,997

(22) Filed: Dec. 20, 2011

(65) Prior Publication Data

US 2012/0152842 A1 Jun. 21, 2012

Related U.S. Application Data

(60) Provisional application No. 61/425,036, filed on Dec. 20, 2010.

(30) Foreign Application Priority Data

Dec. 20, 2010 (EP) .................................. 10015828

(51) Int. Cl.
| | | |
|---|---|---|
| *B01D 61/30* | (2006.01) | |
| *B01D 61/32* | (2006.01) | |
| *A61M 1/36* | (2006.01) | |
| *A61M 1/34* | (2006.01) | |

(52) U.S. Cl.
CPC ........... *A61M 1/3643* (2013.01); *A61M 1/3434* (2013.01)

(58) Field of Classification Search
CPC ............ A61M 1/3643; A61M 1/3621; A61M 1/3465; A61M 1/3434; A61M 1/3644
See application file for complete search history.

(56) References Cited

U.S. PATENT DOCUMENTS

| | | | |
|---|---|---|---|
| 4,324,662 | A | 4/1982 | Schnell |
| 5,259,961 | A | 11/1993 | Eigendorf |
| 5,490,925 | A | 2/1996 | Eigendorf |
| 5,650,071 | A | 7/1997 | Brugger et al. |
| 5,651,893 | A | 7/1997 | Kenley et al. |
| 5,690,831 | A | 11/1997 | Kenley et al. |
| 5,702,606 | A | 12/1997 | Peter, Jr. et al. |
| 5,776,091 | A | 7/1998 | Brugger et al. |
| 5,776,345 | A | 7/1998 | Truitt et al. |
| 5,863,421 | A | 1/1999 | Peter, Jr. et al. |
| 5,895,368 | A | 4/1999 | Utterberg |
| 6,132,616 | A | 10/2000 | Twardowski et al. |
| 6,277,272 | B1 | 8/2001 | Nikaido et al. |
| 6,290,665 | B1 | 9/2001 | Utterberg |
| 6,331,252 | B1 | 12/2001 | El Sayyid et al. |
| 6,551,513 | B2 | 4/2003 | Nikaido et al. |

(Continued)

FOREIGN PATENT DOCUMENTS

| | | |
|---|---|---|
| DE | 34 42 744 A1 | 6/1986 |
| DE | 100 11 208 C1 | 9/2001 |

(Continued)

*Primary Examiner* — John Kim
(74) *Attorney, Agent, or Firm* — K&L Gates LLP

(57) ABSTRACT

A blood treatment system is primed with a replacement liquid that flows directly into the access line of the blood circuit. The replacement liquid may be replacement fluid or blood stored in the replacement bag or the pre-blood pump (PBP) bag. These replacement liquids from the replacement and PBP bags are also used during blood treatment. These replacement liquids are blood or a replacement fluid and, particularly, have electrolyte levels the same as or similar to the electrolyte levels in the vascular blood of the patient.

5 Claims, 4 Drawing Sheets

(56) References Cited

U.S. PATENT DOCUMENTS

| | | |
|---|---|---|
| 6,582,604 B2 | 6/2003 | Nikaido et al. |
| 7,588,722 B2 | 9/2009 | Chevallet |
| 7,794,419 B2 | 9/2010 | Paolini et al. |
| 2002/0032398 A1 | 3/2002 | Steele et al. |
| 2003/0083901 A1 | 5/2003 | Bosch et al. |
| 2003/0163077 A1 | 8/2003 | Kim et al. |
| 2003/0204127 A1 | 10/2003 | Rawles et al. |
| 2004/0149656 A1 | 8/2004 | Rovatti |
| 2006/0173395 A1 | 8/2006 | Brugger et al. |
| 2007/0185430 A1 | 8/2007 | Brugger et al. |
| 2008/0214981 A1 | 9/2008 | Delnevo et al. |
| 2008/0237128 A1 | 10/2008 | Rovatti et al. |
| 2009/0101576 A1 | 4/2009 | Rohde et al. |
| 2009/0114593 A1 | 5/2009 | Fischer |
| 2010/0181235 A1 | 7/2010 | Fava et al. |
| 2010/0219129 A1 | 9/2010 | Bene et al. |
| 2010/0256547 A1 | 10/2010 | Ribolzi et al. |

FOREIGN PATENT DOCUMENTS

| | | |
|---|---|---|
| EP | 0 161 686 A2 | 11/1985 |
| EP | 0 366 950 A1 | 5/1990 |
| EP | 0 560 368 A2 | 9/1993 |
| EP | 1 295 617 A1 | 3/2003 |
| EP | 1 457 218 A1 | 9/2004 |
| EP | 1 880 740 A2 | 1/2008 |
| EP | 2 133 107 A1 | 12/2009 |
| WO | 96/40320 A1 | 12/1996 |
| WO | 01/07136 A1 | 2/2001 |
| WO | 02/098491 A1 | 12/2002 |
| WO | 2008/125894 A1 | 10/2008 |

US 9,095,664 B2

METHOD AND SYSTEM FOR PROVIDING PRIMING AND RESTITUTION LIQUIDS FOR AN EXTRACORPOREAL BLOOD TREATMENT

CROSS RELATED APPLICATION

This application claims the benefit of application Ser. No. 61/425,036 filed Dec. 20, 2010, and European Application No. 10015828.6 filed Dec. 20, 2010 which both are incorporated in their entirety by reference.

BACKGROUND OF THE INVENTION

The present invention relates to supplying priming and restitution liquids to extracorporeal blood treatment systems.

The blood and other liquid passages, e.g., the blood and dialysate circuits, in extracorporeal blood treatment systems are primed by being filled with an isotonic fluid, which is typically a sterile saline solution. Priming rinses the blood and dialysate circuits with saline solution, and purges air and particles from these circuits.

Priming liquids are used to prepare extracorporeal blood treatment to receive and treat blood from patients. The priming liquid flows from the bag through the blood and effluent lines, e.g., flexible plastic tubes, of the blood circuit in the blood treatment system. The priming liquid purges air and particles from the lines. Air in the lines could hinder the pumping operation of the system and to avoid infusing air bubbles into the vascular system of the patient. Particles in the lines could clog the blood access device during infusion.

FIG. 1 shows a conventional blood treatment system coupled to a priming bag 12 filled with a saline solution. The priming bag is connected to a pumping and controller console 14 for the system 10. The priming bag is typically a flexible bag sealed to prevent the entry of air and environmental contaminants to the sterile saline solution in the bag. FIG. 1 illustrates a conventional approach to priming the blood treatment system.

The blood circuit is typically primed before blood is withdrawn from the patient 36 into the blood treatment system 10. To prime the blood circuit, a nurse or other medical professional connects the priming bag 12 to the access line 16, e.g., a blood withdrawal tube, for the blood circuit. After priming, the access line is disconnected from the priming bag and connected to the patient 36.

The priming bag 12 is connected to an inlet of a Y-connector 17 that is also connected to the access line 16 and effluent line 42 of the blood treatment system 10. A peristaltic blood pump 18 (such as a roller pump) moves priming liquid from the bag 12, through Y-connector 17, the access line 16 and to a blood inlet port 20 at a lower end of a blood chamber 24 in a blood treatment device 22. The priming liquid flows up through a blood chamber 24, out a blood outlet port 26, and through a blood line 28, a de-aeration chamber 30, a return line 32 and to a collection bag 34.

The flow through the access line 16, blood chamber 24, blood line 28, de-aerator 30 and return line 32 corresponds to the blood circuit, e.g., blood flow passage, through the extracorporeal blood treatment device. In other blood treatment systems, the blood circuit may include other components and have other configurations. For example, the blood may flow downward direction in other types of blood treatment devices. A common characteristic of the blood circuit is that it represents a flow path of blood withdrawn from the patient, through the blood treatment device and returned to the patient.

The dialysate circuit is also conventionally primed with priming liquid from the priming bag 12, which may be the same as or a separate priming bag as used to prime the blood circuit. The priming liquid is pumped from the bag 12 by an effluent peristaltic pump 40 (rotating in a direction opposite to the rotation during blood treatment) through the effluent line 42 and into an effluent port 44 of an dialysate/effluent chamber 46 in the blood treatment device 22. The priming liquid flows through a dialysate/effluent chamber and out a dialysate port 48 of the blood treatment device 22. The priming liquid flows from the dialystate port, through a blood line 50 coupled to a three-way valve 52 directing the priming liquid to the de-aeration chamber 30, the return line 32 and the collection bag 34. A portion of the priming fluid may pass through a semipermeable membrane between the effluent chamber 46 and the blood chamber 24, and into the blood circuit while priming the dialysate circuit.

Similar conventional liquid priming processes may be performed using the liquids in the replacement liquid bag 54 which is pumped by a replacement peristaltic pump 56; the dialysate bag 58 which is pumped via line 59 by the dialysate peristaltic pump 60, and the pre-blood liquid bag 62 which is pumped by the pre-blood pump (PBP) 64. The upper three-way valve 52 and lower three-way valve 68 are switched during the priming operations to ensure that liquids fill all infusion lines associated with the infusion pumps and to avoid pumping air bubbles into the return line 32 when connected to the patient 36. The infusion lines do not include the access line, associated blood lines and blood treatment device.

After the blood treatment system 10 has been primed, the access line 16 is disconnected from the priming bag 12 and connected to withdraw blood from the patient 36, the return line 32 is disconnected from the collection bag 34 and connected to infuse blood and other liquids into the patient, and the effluent line 42 is disconnected from the priming bag 12 and connected to the collection bag 34.

The priming liquid bag 12 is typically discarded after the blood treatment system is primed. The priming bag is typically used only to prime the blood treatment system. Given the limited use of the priming bag, it represents an additional complexity to blood treatment systems, requires that additional supplies be stored for the system and could result in a delay of treatment if a priming liquid bag is not readily available.

Priming liquid may remain in the blood circuit when the blood treatment system is switched to a blood treatment mode. While the priming liquid is typically a saline solution that may be safely infused into a patient, there is a risk that in certain cases the infusion of the saline solution could upset the electrolyte balance in the patient. One such case is when the patient is a small child. Examples of conventional priming systems and method for extracorporeal blood treatment systems include U.S. Patent Application Publication 2008/0237,128 entitled "Process and Apparatus for Filling and/or Rinsing An Extracorporeal Blood Circuit"; U.S. Patent Application Publication 2009/0101576 entitled "Priming and Air Removal Systems and Methods for Dialysis", and EP 1 457 218 A1 entitled "Automatic Apparatus for Blood Dialysis and Priming Method Using the Apparatus."

Priming techniques have been proposed that use the dialysate liquid to prime an extracorporeal circuit in U.S. Pat. No. 5,259,961 (see also EP 0 560 368 A2) entitled "Method and Assembly for the On-Line Flushing and Filling of an Extracorporeal Blood Circulation System of Dialysis Machines"; U.S. Pat. No. 5,490,925 entitled "Assembly for the On-Line Flushing and Filling of an Extracorporeal Blood Circulation System of Dialysis Machines"; U.S. Pat. No. 6,132,616 entitled Method for Flushing and Filling of an Extracorporeal Blood Circulation System of a Dialysis Machine", and U.S. Pat. No. 6,582,604 entitled "Method of Cleaning and Priming Dialysis System." These techniques generally apply pressure in the blood treatment device to move dialysate liquid across the semipermeable membrane to fill and prime the blood circuit.

BRIEF DESCRIPTION OF THE INVENTION

The priming bag is conventionally used solely to provide priming liquid and is separate from the other liquid filled bags used in a blood treatment system. Conventional priming bags increase the complexity of a blood treatment system because they must be stored, located to prime the system, connected to the blood console separately from other fluid bags and later discarded.

The techniques mentioned above that use dialysate as the priming fluid have disadvantages in that they require moving the dialysate across the semipermeable membrane in the blood treatment device which may be a slow process, can expose the dialysate to the atmosphere and fill the blood circuit with dialysate such that undiluted dialysate could potentially be infused into the vascular system.

A novel approach to priming a blood treatment system is to prime the blood circuit of the system with extracorporeal blood or other replacement liquids that may be infused to supplement the blood in the blood stream of a patient. For proposes of this application, the term "replacement liquid" means extracorporeal blood, replacement blood, substitute blood and other fluids that flow through the return line of the blood circuit to supplement the blood stream of the patient. The priming liquid may be, for example, a replacement fluid stored in the replacement bag or the pre-blood pump (PBP) bag. These blood liquids from the replacement and PBP bags are used during blood treatment. These replacement liquids in the PBP bag, replacement bag and possibly other bags will typically have electrolyte levels the same as or similar to the electrolyte levels in the vascular blood of the patient.

During priming of the blood treatment system, the liquid in the PBP bag or replacement bag flows as priming liquid to prime the blood and dialysate circuits. Returned priming liquid flows to the collection bag. Using the PBP or replacement bags as a source of priming liquid eliminates the need to find and connect a separate and dedicated priming liquid bag(s) to the blood treatment console. Further, the liquids from the PBP and replacement bags that remain in the blood circuit as a result of priming may be infused into the patient without concern that the liquid will disrupt the electrolyte levels of the patient.

A method has been conceived and is disclosed herein for an extracorporeal blood treatment system including: a pumping console having a source of a replacement fluid, a first pump, a blood pump and a collection vessel and a blood circuit including an access line, a blood treatment device, a return line and a source line from the source, the method comprising the steps of: coupling the blood circuit to the console including mounting the access line onto the blood pump and mounting the source line to the first pump; connecting the access line to the source and connecting an outlet of the return line to a collection vessel, and priming the blood circuit by pumping with the first pump the replacement fluid from the source into the access line to fill the blood circuit with the replacement fluid, wherein the collection vessel receives the replacement fluid from the blood circuit.

The priming step may further comprise pumping by the blood pump the replacement fluid through the access line simultaneously with the pumping by the first pump of the replacement fluid. The step of simultaneously pumping may include the blood pump pumping in a first direction to move the replacement fluid through the access line to the collection vessel, and the method further comprising, after the priming, the blood pump pumping in a second direction, opposite to the first direction, blood withdrawn from the patient through the access line and through the blood circuit. The step of simultaneously pumping may include the blood pump having a pumping rate slower than a pumping rate of the first pump.

The first pump may include a replacement fluid pump and the source includes a replacement fluid bag. The priming step may further comprise pumping a replacement fluid through an effluent line, an effluent chamber of the blood treatment device, the return line, and to the collection vessel. The replacement fluid pumped through the effluent line may be preblood drawn from a PBP bag.

The source may be a PBP bag and the method further includes clamping the access line downstream of a junction between the access line and a line connected to the PBP bag, wherein first pump is a PBP pump, and the PBP pump and the blood pump at substantially the same pumping rate during the priming step.

A method has been conceived and is disclosed herein for an extracorporeal blood treatment system including: a pumping console having a source of a replacement fluid, a first pump, a blood pump and a collection vessel and a blood circuit including an access line, a blood treatment device, a return line and a source line from the source, the method comprising the steps of: coupling the blood circuit to the console including mounting the access line onto the blood pump and mounting the source line to the first pump; connecting the access line to the source and connecting an outlet of the return line to a collection vessel, and priming the blood circuit by pumping with the first pump the replacement fluid from the source into the access line to fill the blood circuit with the replacement fluid, wherein the collection vessel receives the replacement fluid from the blood circuit.

The priming step may further comprise pumping by the blood pump the replacement fluid through the access line simultaneously with the pumping by the first pump of the extracorporeal blood. The step of simultaneously pumping may include the blood pump pumping in a first direction to move the replacement fluid through the access line to the collection vessel, and the method further comprising, after the priming, the blood pump pumping in a second direction, opposite to the first direction, blood withdrawn from the patient through the access line and through the blood circuit. The step of simultaneously pumping by the blood pump may include the blood pump having a pumping rate slower than a pumping rate of the first pump.

The first pump may include a replacement fluid pump and the source includes a replacement fluid bag. The priming step may further comprise pumping the replacement fluid through an effluent line, an effluent chamber of the blood treatment device, the return line, and to the collection vessel. The replacement fluid may be preblood drawn from a PBP bag. The method may further include clamping the access line downstream of a junction between the access line and a line connected to the PBP bag, wherein first pump is a PBP pump, and the PBP pump and the blood pump at substantially the same pumping rate during the priming step.

The method may further include, after the priming step, disconnecting the access line from the source of replacement fluid and disconnecting the return line from the collection vessel, and connecting the access line and the return line to a vascular system of a patient and infusing the patient with the replacement fluid from the source.

A method has been conceived and is disclosed to prime an extracorporeal blood treatment system including a source of replacement fluid, a first pump, a blood pump, a collection vessel, an access line, a blood treatment device and a return line, the method comprising the steps of: priming the extracorporeal blood treatment system by the first pump pumping the replacement fluid from the source to the access line coupled to the blood pump; the priming including simultaneously with the pumping by the first pump, pumping the replacement fluid by the blood pump through the access line and to the collection vessel, and filling with the replacement fluid the access line, a blood chamber in the blood treatment device and the return line which is connected to the collection vessel.

The step of simultaneously pumping may include pumping by the blood pump in a first direction to move the replacement fluid to the collection vessel, and the method further comprising, after the priming, the blood pump pumping in a second direction, opposite to the first direction, blood withdrawn from the patient into the access line and to the blood chamber. The step of simultaneously pumping may include the blood pump having a pumping rate slower than a pumping rate of the first pump.

The first pump may include a replacement fluid pump and the source of replacement fluid may include a replacement fluid bag. The priming may further comprise pumping the extracorporeal blood through an effluent line, an effluent chamber of the blood treatment device, the return line and into the collection vessel. The replacement fluid may be preblood drawn from a PBP bag. The source of replacement fluid may include at least one bag connected to a pumping console of the blood treatment system. The source of the replacement fluid may be a PBP bag, and the method further may include clamping the access line downstream of a junction between the access line and a line connected to the PBP bag, wherein the first pump is a PBP pump and the PBP pump and the blood pump at substantially the same pumping rate during the priming step.

The method may further comprise, after the priming, disconnecting the access line from the source of replacement fluid and disconnecting the collection vessel from the return line, and connecting the access line and the return line to a vascular system of a patient wherein the patient is infused with the replacement fluid remaining in the blood circuit.

An extracorporeal blood treatment console has been conceived and is disclosed herein including at least a first pump, a blood pump and a controller, wherein the console is adapted to receive a blood treatment device including a blood chamber, an effluent chamber and a semipermeable membrane separating the chambers, and the controller primes the extracorporeal blood treatment system by controlling: the first pump to pump a replacement fluid from a source to an access line coupled to the blood pump, and simultaneously with the pumping by the first pump, the blood pump pumps the replacement fluid through the access line and into a collection vessel, wherein the pumping of the first pump and the blood pump fills the blood chamber and the return line which is connected to the collection vessel, with the replacement fluid.

The controller may control the blood pump to pump in a first direction to move the replacement fluid to the collection vessel, and, thereafter, control the blood pump to pump in a second direction, opposite to the first direction, blood withdrawn from a patient through the access line and into the blood chamber. The controller may control the blood pump to pump at a pumping rate slower than a pumping rate of the first pump during the simultaneous pumping. The first pump may include a replacement fluid pump and the source of extracorporeal blood includes a replacement fluid bag. The controller may control an effluent pump to pump the replacement fluid through an effluent line, through the effluent chamber, to the return line and into the collection vessel. The source of extracorporeal blood may include at least one bag connected to a pumping console of the blood treatment system.

A connection assembly has been conceived and is disclosed herein for an extracorporeal blood treatment system comprising: a first multi-branched connector having internal fluid passages connecting a first port connectable to an effluent line of the system, a second port connectable to an access line of the system and a third port connectable to a first port of a second multi-branched connector, and the second multi-branched connector having internal fluid passages connecting the first port, a second port connectable to a return line of the extracorporeal blood treatment system and a third port connectable to a collection bag. The multi-branched connectors may each be Y-connectors.

A method has been conceived and is disclosed herein to provide restitution blood to a patient using a blood treatment system including: (i) a pumping console having a source of restitution blood, a restitution pump, a blood pump and a collection vessel, and (ii) a blood circuit including an access line, a blood treatment device, a return line and a restitution source line extending from the source, the method comprising the steps of: coupling the blood circuit to the console including mounting the access line to the blood pump and mounting the restitution line to the restitution pump; connecting the access line to the source of the restitution blood and connecting an outlet of the return line to a collection vessel; and connecting the return line to a vascular system of a patient to receive the restitution blood from the source.

An apparatus has been conceived and is disclosed for extracorporeal blood treatment comprising: an extracorporeal blood treatment console including at least a first pump, a blood pump and a controller; a blood treatment device including a blood chamber, an effluent chamber and semipermeable membrane separating the chambers; a blood circuit including a blood line and a blood return line wherein both of said lines are in fluid communication with the blood chamber of the blood treatment device, and the blood access line is acted on by the blood pump to move blood withdrawn from a patient through the blood circuit during blood treatment; an effluent line coupled to the effluent chamber and providing a passage for effluent from the effluent chamber to flow to a collection vessel during blood treatment; a source of a replacement fluid connected by a source line to the blood circuit; the controller controlling the first pump and the blood pump, the controller including a non-transitory memory and a processor executing program instructions for stored in the memory, the execution of the program instructions causes the controller to prime the extracorporeal blood treatment system by controlling: the first pump to pump the replacement fluid from the source to the access line coupled to the blood pump, and simultaneously with the pumping by the first pump, the blood pump to pump the replacement fluid through the access line and into the collection vessel, wherein the pumping of the first pump and the blood pump fills the blood chamber and the return line with the replacement fluid.

After the priming step, the method may include disconnecting the access line from the source of replacement fluid and disconnecting the return line from the collection vessel, and connecting the access line and the return line to a vascular system of a patient and infusing the patient with the extracorporeal blood or replacement fluid from the source.

BRIEF DESCRIPTION OF DRAWINGS

The description will be made with reference to the accompanying figures of the drawings, provided by way of non-limiting example, in which.

DETAILED DESCRIPTION OF THE INVENTION

Figure 2:
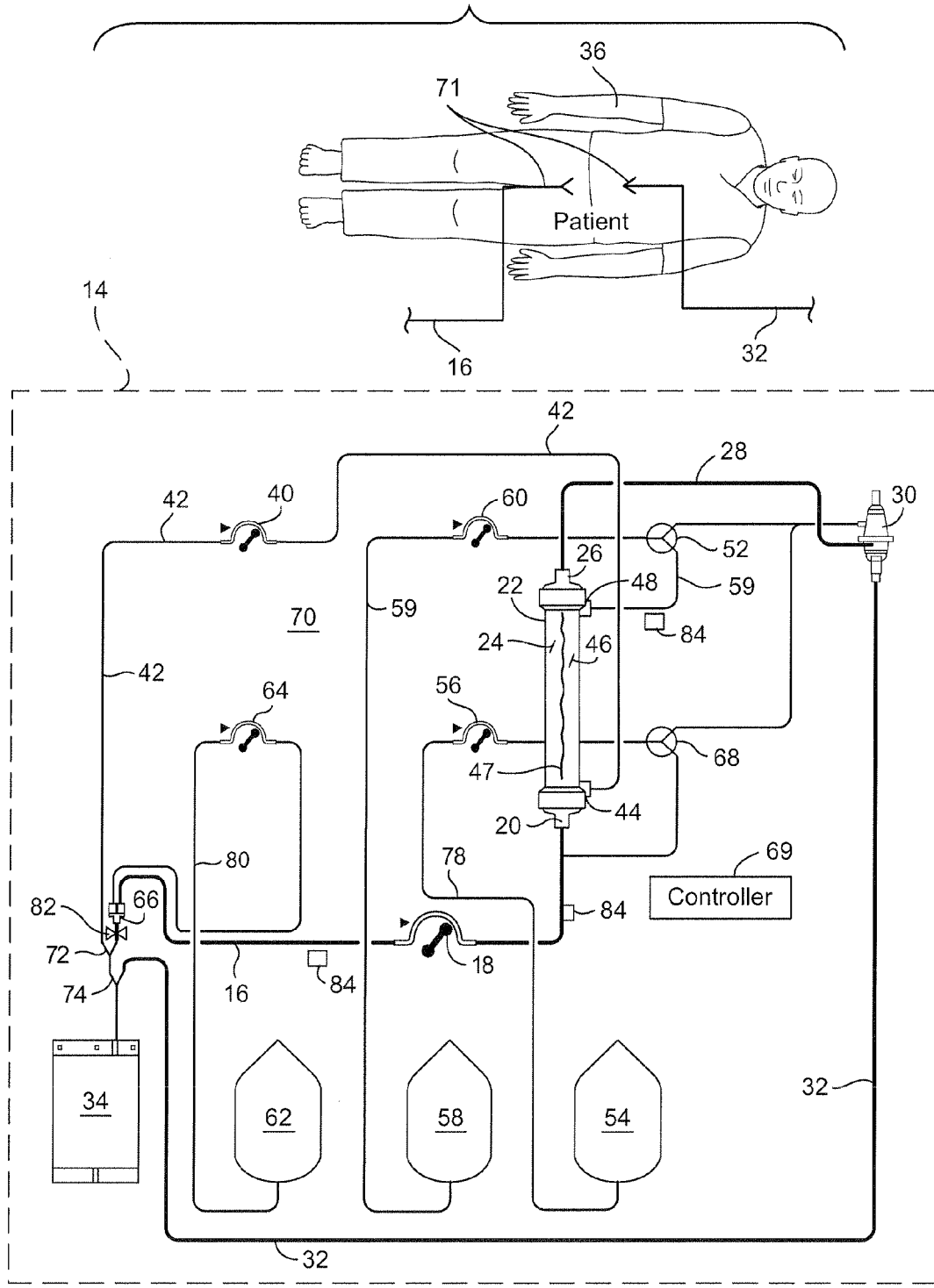
FIG. 2 is a schematic diagram of an exemplary blood treatment system in which the source of priming liquid is a PBP or replacement bag.

FIG. 2 is a schematic diagram of an exemplary blood treatment system 70 in which the source of priming liquid is the PBP bag 62 or replacement bag 54. A separate bag used solely to provide priming liquid is not necessary to prime the system. Further, the priming liquid is blood or a replacement fluid.

Figure 1:
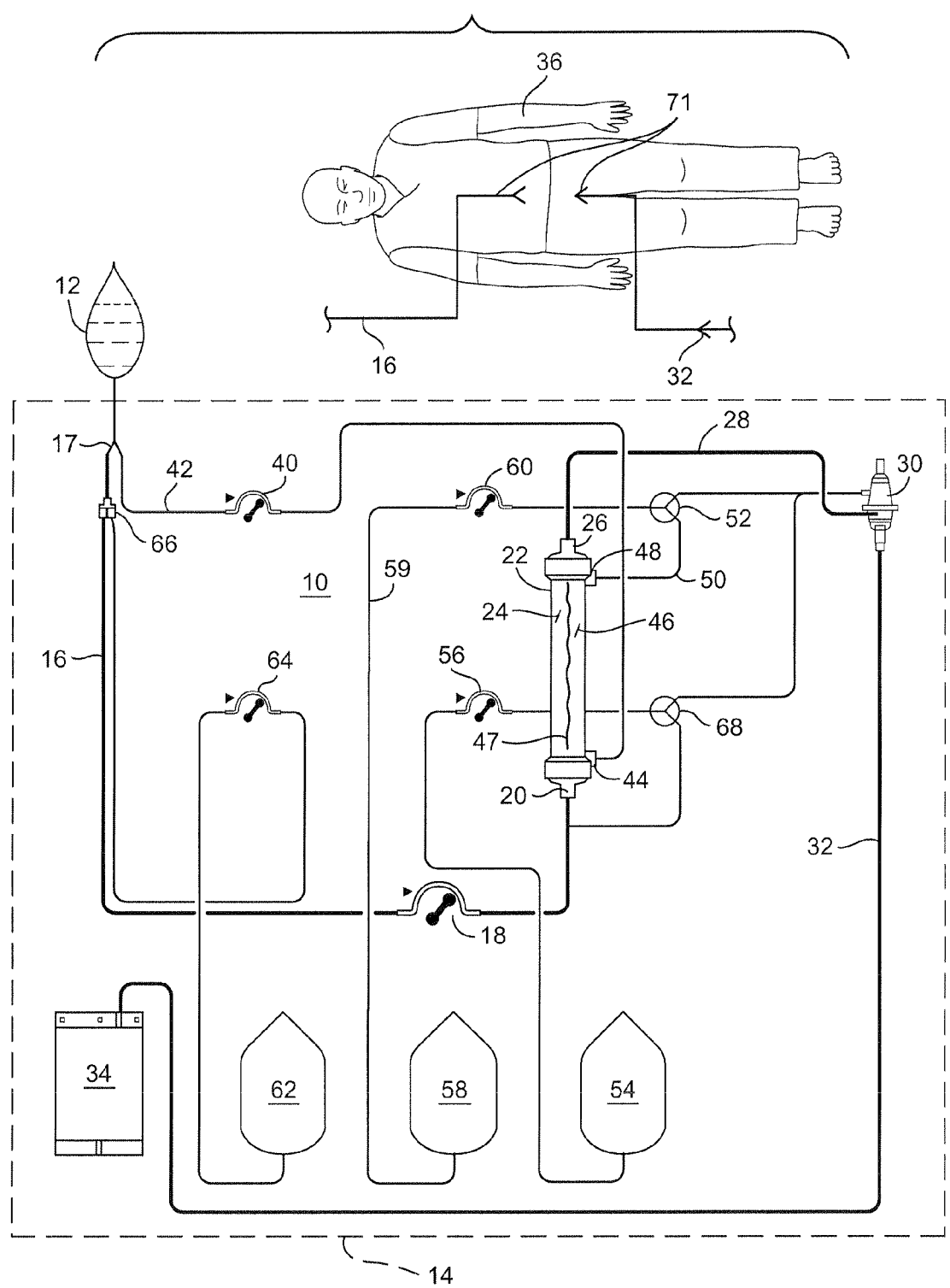
FIG. 1 is a schematic diagram of an exemplary conventional blood treatment system with a source of priming liquid that is separate from the collection bag for returned priming liquid and effluent.

The blood treatment system 70 is similar in many respects to the blood treatment system 10 shown in FIG. 1. Similar components of these systems 10, 70 are identified with common reference numbers in FIGS. 1 and 2.

Blood treatment systems, such as the system 70, may be used to treat blood and infuse treated blood to a patient. The treatments may be without limitation: hemodialysis, hemo(dia)filtration, continual renal replacement therapy (CRRT), therapeutic plasma exchange (TPE), hemoperfusion, molecular adsorbent recirculation, ultrafiltration, cascade hemofiltration, blood collection and other extracorporeal treatment of the blood. The blood treatment system 70 shown in FIG. 2 is tailored for continuous renal replacement therapies (CRRT) and is disclosed herein to illustrate the invention. The priming apparatus and methods disclosed herein may be applied to other types of extracorporeal blood treatment systems to eliminate a need for a separate priming liquid bag and to use blood or a replacement fluid as the priming liquid.

The blood treatment device 22 may be a dialyzer, ultrafiltration filter or other device to treat blood flowing through the extracorporeal blood circuit. The blood treatment device 22 houses a semipermeable membrane 47 that separates the blood chamber 24 from the effluent chamber 46. The membrane and chambers are illustratively shown in blood treatment device shown in FIGS. 1 and 2, and may in actuality be hollow fibers having porous sidewalls. The membrane may have fine pores to prevent passage of blood cells and large molecules.

The blood circuit comprises the passages in the extracorporeal blood treatment system through which blood flows from and to the patient. These passages may include: the access line 16 that is connectable to a needle, catheter or other access device 71 for withdrawing blood from the vascular system of the patient 36; the blood chamber 24 in the blood treatment device 22; a blood line 28 from the blood chamber to the de-aeration chamber 30 (which is included in the blood circuit), and a blood return line 32 that connects to a needle, catheter or other access device 71 for infusing blood to the vascular system of the patient 36.

The dialysate circuit comprises the passages in the extracorporeal blood treatment system through which flows the dialysate liquid. The dialysate circuit may include the dialysate bag 58, dialysate line 59, and the dialysate/effluent chamber 46 of the blood treatment device 22.

During blood treatment, blood withdrawn from a patient flows through the access line and to a lower blood inlet 20 of the blood treatment device where the blood enters the blood chamber 24. In this chamber, the blood may be treated in dialysis by diffusive mass transfer across the semipermeable membrane 47 due to a concentration gradient between the effluent and dialysate chamber 46 and the blood chamber 24. Similarly, the blood may be treated in hemofiltration by having liquid extracted from the blood pass through the semipermeable membrane 47 to the effluent and dialysate chamber 46 and having dialysate liquid from the chamber 46 pass through the membrane 47 to the blood chamber 24.

Dialysate flows through dialysate line 59 and is pumped by peristaltic dialysate pump 60 to an upper port 48 at an upper end of the blood treatment device 22. An upper three-way valve 52 is configured to direct the dialysate into the upper port 48 of the blood treatment device.

While the blood treatment system 70 is in a blood treatment mode, blood flows from the outlet 26 of the blood chamber 24 through the blood line 28 to the de-aeration chamber 30 which ensures that air bubbles are not entrained in the blood flowing to the return line 32 that infuses blood through an access device 71 to the vascular system, e.g., a vein or artery, of the mammalian patient 36, such as a human.

During the blood treatment mode, replacement fluid from bag 54 may be pumped by a replacement peristaltic pump 56 through line 78 to merge with blood to be infused in the patient. A lower three-way valve 68 determines whether the replacement fluid passes through the blood chamber 24 of the blood treatment device 22 or flows directly to the de-aeration chamber 30 and return line 32. Further, the replacement fluid liquid from the RBP bag 62 may be pumped by the RPB pump 64 to via line 80 and coupling 66 to the access line 16 and thereby flow into the blood circuit.

A controller 69 mounted in the console 14 includes a non-transitory computer memory and a processor executing instructions for controlling the pumps based on, for example, weight data generated by weight scales measuring the weight of one or more of the fluid filled bags 12, 34, 54, 58 and 62, and use input settings and other data collected during the priming and blood treatment modes of the blood treatment system 70.

Prior to blood treatment, the blood circuit and the dialysis circuit are primed. Initially, the liquid filled replacement bag 54, dialysate bag 58 and PBP bag 62 are connected to the blood treatment console 14 and the lines 78, 59 and 80 for these bags are connected to their respective pumps 56, 60 and 64.

Figure 3:
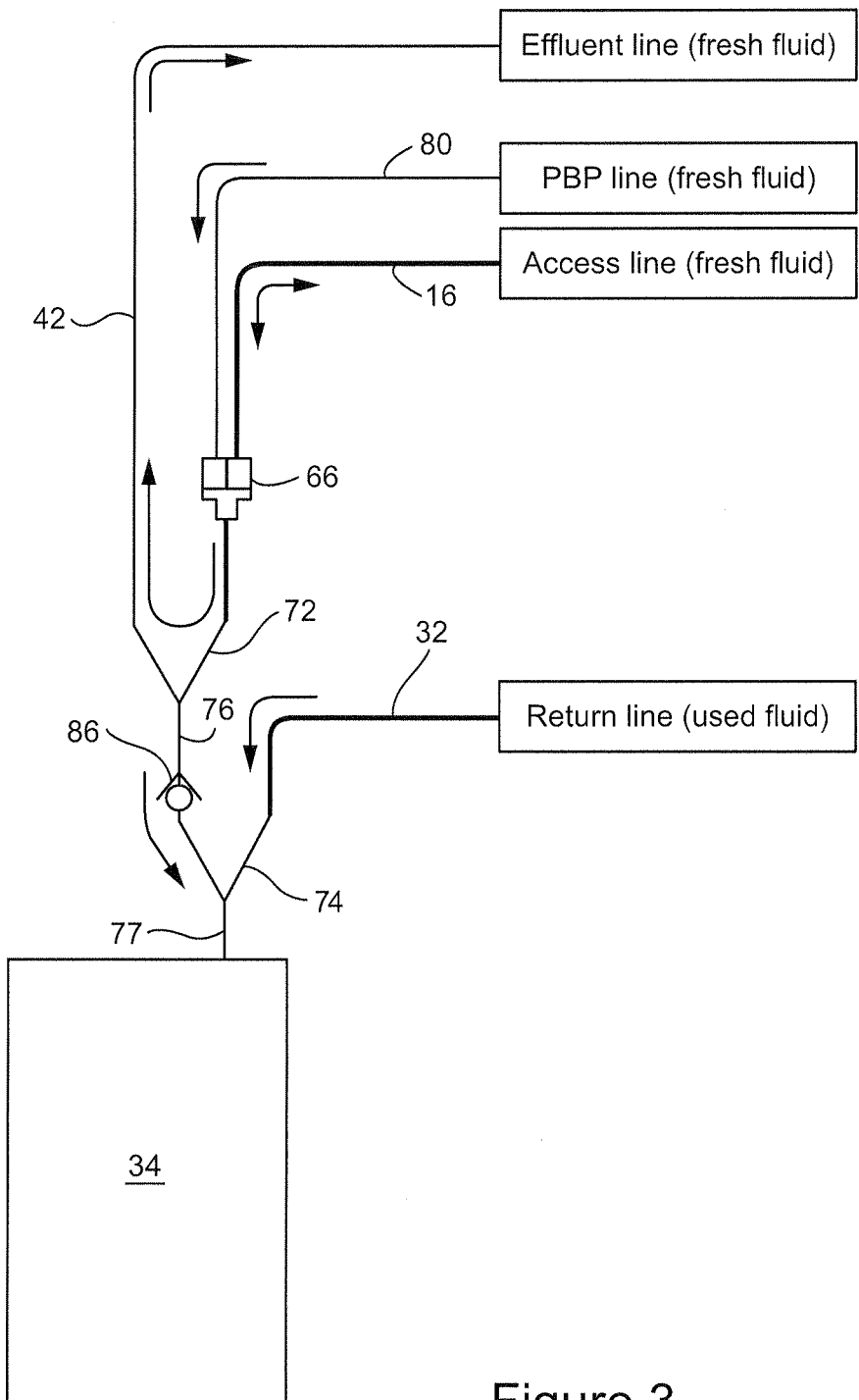
FIG. 3 is a schematic diagram of an exemplary arrangement of Y-connectors arranged to connect various lines in the blood treatment system to each other and the collection bag during the priming process.

For purposes of priming the blood and dialysate circuits, a first Y-connector 72 is assembled in series with a second Y-connector 74 and attached to the collection bag 34. As shown in FIGS. 2 and 3, the access line 16 and effluent line 42 are each connected to a respective branch of the first Y-connector 72. The third branch 76 of the first Y-connector is coupled to a first branch of the second Y-connector 74. Another branch of the second Y-connector 74 is attached to the return line 32 and the third branch 77 of the second Y-connector drains to the collection bag 34. The two Y-connectors 72, may be configured as distinct connector components that are connected together, or as a single flow direction component comprising four or more branches each directing fluid in a manner similar to the connectors 72, 74.

The flow passages through each of the Y-connectors 72, 74 are open and allow liquids to flow through each branch of the connectors. The direction of flow through each of the connectors may be controlled by operation of the pumps and particularly, the blood pump 18, effluent pump 40 and pre-blood pump 64. An optional check valve or other one-way flow device 86 may be connected to the third branch of the first Y-connector to prevent the flow of returned priming liquid into the effluent line 42 or access line 16.

To prime the blood circuit, the replacement pump 56 pumps replacement fluid from the replacement bag 54 through the replacement line 78. The lower three-way valve 68 is set to direct the replacement fluid to the access line 16. The replacement pump may turn in a clockwise direction and be set in a pre-dilution mode.

During an initial period of priming, the blood pump 18 rotates in a counter-clockwise direction (opposite to the pump rotation during blood treatment) to force replacement fluid entering the access line to flow past the blood pump and fill the entirety of the access line. Air in the access line may be pushed into the collection bag while the blood pump is rotating counter-clockwise. The blood pump rotates at a slower rate than the replacement pump to avoid drawing air from the collection bag 34 into the return line and blood treatment device, or drawing fluid from the blood treatment device into the access line. The upper three-way valve 52 and lower three-way valve 68 are switched during the priming operations to ensure that liquids fill all lines and to avoid pumping air bubbles into the return line 32 when connected to the patient 36.

After the access line has been primed with the replacement liquid, the blood pump is temporarily stopped to prevent further flow through the access line. While the blood pump is stopped and during the blood circuit priming process, the replacement pump 56 continues to move replacement liquid into the access line 16 so that the liquid fills the blood chamber 24 and flows into the blood line 28. The lower three-way valve 68 is set to direct the replacement liquid directly to the access line 16 and not allow the liquid to flow directly to the de-aerator. The replacement liquid fills the blood line 28, passes through the de-aerator 30 which removes air bubbles in the liquid and flows through the return line 32 to the collection bag. The upper three-way valve 52 is set such that the upper port 48 is open only to the dialysis line 59 which is clamped closed by the stopped dialysis pump 60.

As an alternative to using the replacement fluid as the priming liquid, the blood in the PBP bag 62 may be used to prime the blood circuit. To use the PBP bag 62 to prime the blood circuit, the PBP pump 64 pumps the PBP blood liquid through the PBP line and into the inlet to access line 16 via the coupling 66. At the same time, the blood pump 18 is pumping the PBP liquid through the access 16. The blood pump 18 moves the PBP liquid at a slightly slower rate than the rate at which the PBP pump moves the liquid to avoid suction of air from the collection/effluent bag 34. The combined pumping action of the PBP and blood pumps 18, 64 move the PBP liquid through the remainder of the access line, the blood chamber 24, blood line 28, de-aerator 30 and the return line 32, from which the PBP liquid flows into the collection bag 34.

To prime the dialysate circuit, the PBP liquid is pumped by the PBP pump 64 through the PBP line 80 and to the effluent line 42 via the first Y-connector 72. The effluent pump 40, which is pumping at a rate slightly less than the PBP pump, moves the PBP fluid to the lower port 44 to fill the effluent/dialysis chamber 46. By setting the upper three-way valve 52 to a neutral position the RBP fluid flows from the port 48 through the de-aeration chamber 30 and to the return line 32 and the collection bag 34.

Figure 4:
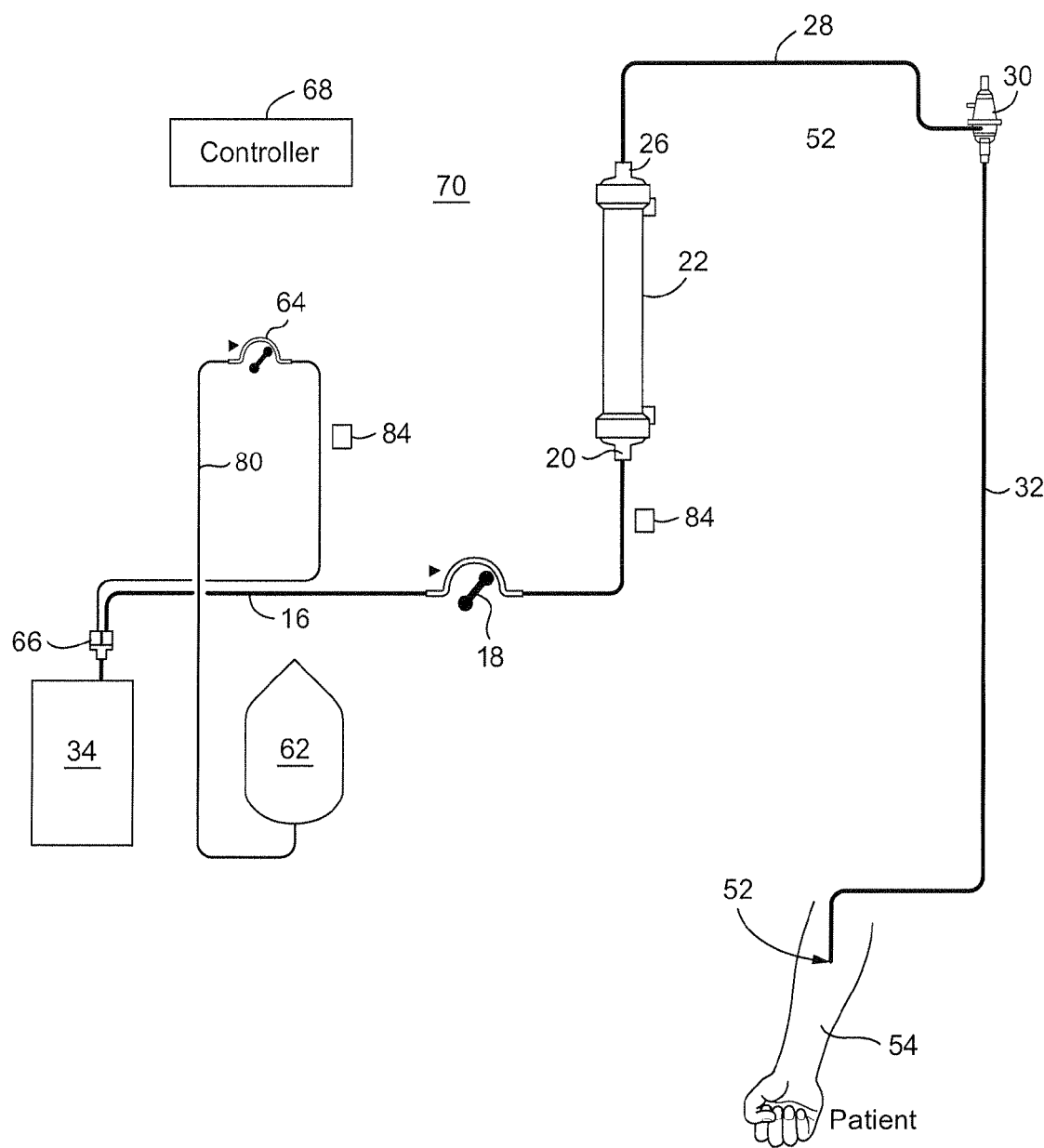
FIG. 4 is a schematic diagram of a portion of the blood treatment system which is configured to pump liquid from the restitution blood vessel to the patient.

FIG. 4 is a schematic diagram of a portion of the blood treatment system 70 which is configured to pump liquid from the PBP bag 62 as restitution blood into the patient 54. Blood restitution typically requires about 200 ml of blood liquid. A separate source of restitution blood is not necessary with the configuration shown in FIG. 4.

The effluent line is disconnected from the collection bag 34 and replaced by connecting the inlet to the access line 16 to the collection bag. The PBP pump 64 pumps liquid from the PBP bag 62 to the access line 16 via coupling 66. As the PBP liquid flows through the access line the blood pump 18 also pumps the liquid to the lower blood inlet 20 of the blood treatment device 22 and from the upper blood outlet 26, through blood line 28, past the de-aerator 30 and to the return line 32 which is connected to an access device 52 to infuse the PBP blood into the vascular system of the patient. All of the blood in the blood circuit may be infused to the patient, except for a small volume, such as three milliliters, of the blood remaining in the junction between the access and PBP lines. This small amount of blood drains to the collection bag.

The blood pump 18 pumps at a slightly slower rate than the PBP pump 64 to avoid drawing liquid from the collection bag into the blood circuit.

Alternatively, the restitution PBP blood may be infused without disconnecting the effluent line 42 from the collection bag. Rather than connecting the access line to the collection bag, the branch of the Y-connector 72 connected to the access line 16 is clamped shut, such as with a clamp 82 shown in FIG. 2. Because the branch of the Y-connector 72 clamped, the liquid from the PBP bag 62 flowing from the PBP line 80 must flow through, junction 66, to the access line 16 and into the blood chamber 24 of the blood treatment device. The blood and PBP pumps 18, 64 operate at the same rate to ensure that all of the PBP liquid flows through the lines 16 and 80 without excessive suction or pressure in these lines.

Pressure sensors 84 may monitor the liquid pressure in these lines and blood treatment device, and a controller for the blood treatment device may adjust the relative pumping speeds of the PBP and blood pumps to maintain the pressures in the PBP and access lines within predetermined pressure ranges.

The priming and restitution methods and systems disclosed herein and illustrated in FIGS. 2 to 4 avoid a need for separate supply bags of priming liquid and restitution blood. By eliminating the need for these liquid supply bags, the setup of the blood treatment device is simplified and requires fewer liquid filled bags. The simplification and reduction in fluid filled bags saves time in setting up the extracorporeal blood treatment system and reduces the complexity of operating the system. Similarly, the risk of contamination occurring as bags are connected to the blood treatment system is reduced because of the reduction in the number of bags to be connected to the system. Further, the conventional saline priming liquid is replaced with a replacement fluid liquid that may be infused into the patient.

While the invention has been described in connection with what is presently considered to be the most practical and preferred embodiment, it is to be understood that the invention is not to be limited to the disclosed embodiment, but on the contrary, is intended to cover various modifications and equivalent arrangements included within the spirit and scope of the appended claims.

What is claimed is:

1. A method for an extracorporeal blood treatment system including: (i) a pumping console having a source of a replacement fluid, a first pump, a blood pump and a collection vessel (ii) a blood circuit including an access line, a blood chamber of a blood treatment device having a semipermeable membrane separating the blood chamber from an effluent chamber of the blood treatment device, a return line, and a source line from the source (iii) and a dialysis circuit including a dialysate line the effluent chamber of the blood treatment device, and an effluent line, the method comprising the steps of:

coupling the blood circuit to the console including mounting the access line onto the blood pump and mounting the source line to the first pump;

connecting the access line to the source of the replacement fluid and connecting an outlet of the return line to a collection vessel;

priming the blood circuit by pumping with the first pump the replacement fluid from the source into the access line to fill the blood circuit with the replacement fluid, wherein the collection vessel receives the replacement fluid from the blood circuit; and priming the dialysis circuit by pumping the replacement fluid through the effluent line, the effluent chamber of the blood treatment device, the dialysate line and the return line, to the collection vessel.

2. The method of claim 1 wherein said priming the blood circuit further includes, simultaneously with said pumping with the first pump, pumping with the blood pump the replacement fluid through the access line.

3. The method as in claim 2 wherein the step of simultaneously pumping includes the blood pump pumping in a first direction to move the replacement fluid through the access line to the collection vessel, and the method further comprising, after the priming of the blood circuit, the blood pump pumping in a second direction, opposite to the first direction, blood withdrawn from the patient through the access line and through the blood circuit.

4. The method as in claim 1 wherein the step of simultaneously pumping with the blood pump includes the blood pump having a pumping rate slower than a pumping rate of the first pump.

5. The method as in claim 1 further comprising:

after the priming of the dialysis circuit and the blood circuit, connecting the access line and the return line to a vascular system of a patient and infusing the patient with the replacement fluid.

* * * * *